US 9,950,970 B2

(12) United States Patent
Xu

(10) Patent No.: US 9,950,970 B2
(45) Date of Patent: Apr. 24, 2018

(54) IONIC LIQUID REACTOR WITH HEAT EXCHANGER

(71) Applicant: UOP LLC, Des Plaines, IL (US)

(72) Inventor: Zhanping Xu, Iverness, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/568,331

(22) Filed: Dec. 12, 2014

(65) Prior Publication Data

US 2016/0168046 A1    Jun. 16, 2016

(51) Int. Cl.
*C07C 2/56* (2006.01)
*C07C 2/58* (2006.01)
*B01J 19/00* (2006.01)
*B01J 19/18* (2006.01)

(52) U.S. Cl.
CPC .............. *C07C 2/58* (2013.01); *B01J 19/006* (2013.01); *B01J 19/0066* (2013.01); *B01J 19/18* (2013.01); *B01J 2219/0004* (2013.01); *B01J 2219/00006* (2013.01); *B01J 2219/0011* (2013.01); *B01J 2219/00047* (2013.01); *B01J 2219/0077* (2013.01); *B01J 2219/00081* (2013.01); *Y02P 20/582* (2015.11)

(58) Field of Classification Search
CPC .... C07C 2/56; C07C 2/58; C07C 2/64; C07C 2/66
USPC .......................... 585/911, 721, 722, 457, 461
See application file for complete search history.

(56) References Cited

U.S. PATENT DOCUMENTS

| | | | |
|---|---|---|---|
| 2,416,184 A * | 2/1947 | Lee | C07C 6/123 585/322 |
| 3,696,168 A | 10/1972 | Vanderveen | |
| 5,785,933 A | 7/1998 | Cunningham et al. | |
| 7,432,408 B2 | 10/2008 | Timken et al. | |
| 7,727,925 B2 | 6/2010 | Elomari et al. | |
| 7,951,889 B2 | 5/2011 | Bergman et al. | |
| 8,142,725 B2 | 3/2012 | Hommeltoft et al. | |
| 8,163,856 B2 | 4/2012 | Bergman et al. | |
| 8,183,425 B2 * | 5/2012 | Luo | C07C 2/60 585/714 |
| 8,383,874 B2 | 2/2013 | Strauss et al. | |
| 8,507,396 B2 | 8/2013 | Elomari et al. | |
| 8,524,965 B2 | 9/2013 | Campbell et al. | |
| 8,552,243 B2 | 10/2013 | Liu et al. | |
| 8,692,048 B2 | 4/2014 | Liu et al. | |
| 8,729,329 B2 | 5/2014 | Hommeltoft et al. | |
| 2003/0216604 A1 * | 11/2003 | Ackerman | C07C 2/62 585/715 |
| 2009/0171133 A1 | 7/2009 | Luo et al. | |
| 2011/0282114 A1 | 11/2011 | Luo et al. | |
| 2011/0319693 A1 | 12/2011 | Hommeltoft et al. | |
| 2012/0165593 A1 | 6/2012 | Liu et al. | |
| 2013/0004378 A1 | 1/2013 | Luo et al. | |
| 2013/0066130 A1 | 3/2013 | Luo et al. | |

(Continued)

FOREIGN PATENT DOCUMENTS

WO    WO 2011/015662 A2    2/2011

*Primary Examiner* — Thuan D Dang

(57) ABSTRACT

An ionic liquid reactor and a process for controlling heat generation from an ionic liquid reactor unit. The ionic liquid reactor includes an internal heat exchanger. Impellers break the ionic liquid into small droplets to ensure reactions and mix the fluids to ensure reactions and enhance heat exchanger. Baffles may be used to direct the flow of the fluids within the reactor.

7 Claims, 3 Drawing Sheets

(56) References Cited

U.S. PATENT DOCUMENTS

| | | |
|---|---|---|
| 2013/0066132 A1 | 3/2013 | Cleverdon et al. |
| 2013/0066133 A1 | 3/2013 | Cleverdon et al. |
| 2013/0331625 A1 | 12/2013 | Liu et al. |
| 2014/0066678 A1 | 3/2014 | Timken et al. |
| 2014/0128654 A1 | 5/2014 | Fang et al. |
| 2014/0134065 A1 | 5/2014 | Timken et al. |

* cited by examiner

Section A-A

IONIC LIQUID REACTOR WITH HEAT EXCHANGER

FIELD OF THE INVENTION

This invention relates generally to an ionic liquid reactor and more particularly to an ionic liquid reactor with a heat exchanger.

BACKGROUND OF THE INVENTION

Ionic liquids are essentially salts in a liquid state, and are described in U.S. Pat. No. 4,764,440, U.S. Pat. No. 5,104,840, and U.S. Pat. No. 5,824,832. The properties vary extensively for different ionic liquids, and the use of ionic liquids depends on the properties of a given ionic liquid. Depending on the organic cation of the ionic liquid and the anion, the ionic liquid can have very different properties. The behavior of the ionic liquid varies considerably for different temperature ranges, and it is preferred to find ionic liquids that do not require operation under more extreme conditions such as refrigeration.

Acidic ionic liquid may be used as a catalyst in various chemical reactions, such as for the alkylation of iso-butane with olefins. The alkylation reaction is highly exothermic. To control the temperature, it is common for a portion of the unreacted lighter hydrocarbons to be vaporized. However, controlling the heat by vaporization is undesirable because the vaporization creates difficulties in controlling the reactor operation, the ionic liquid dispersion, and, the acid concentration. Therefore, it is believed to be more desirable to maintain the reactants and products in liquid form.

While it would be desirable to utilize heat exchange to control the temperature, any heat exchanger will need to be configured for minimizing the impact of the ionic liquid phase on heat transfer due to its high viscosity and potential for fouling of the heat transfer surface.

Additionally, as will be appreciated, conjunct polymer is often a byproduct of the various ionic liquid catalyst reactions including but not limited to alkylation, oligomerization, isomerization, and disproportionation. Conjunct polymer is typically highly conjugated, olefinic, highly cyclic hydrocarbons. The conjunct polymer is often associated with ionic liquid and will also impact heat transfer in similar ways as ionic liquid.

It would be desirable to provide an ionic liquid reactor that can effectively control the heat produced by exothermic reactions without the need of vaporization. It would also be desirable for such a reactor to account for the presence of conjunct polymer and ionic liquid catalyst.

SUMMARY OF THE INVENTION

An ionic liquid catalyst reactor and a process for controlling the heat of an ionic liquid catalyst reaction have been invented. The ionic liquid catalyst reactor and process utilize at least one internal heat exchanger to remove the heat produced by the exothermic reactions. The heat exchanger in the reactor is designed to accommodate the ionic liquid catalyst, the hydrocarbons, and the conjunct polymer that have a tendency to foul the equipment.

Therefore, in a first aspect of the present invention, the invention may be broadly characterized as a providing an ionic liquid reactor comprising a shell, at least one impeller disposed within the shell, and, at least one heat exchanger disposed within the shell. The shell comprises an inlet for a hydrocarbon stream, an inlet for an ionic liquid catalyst, and an outlet for effluent. The inlet for ionic liquid catalyst and the inlet for the hydrocarbon stream are disposed proximate a first end of the shell. The outlet for effluent is disposed proximate a second end of the shell.

In some embodiments, the ionic liquid reactor further comprises at least one heat exchanger comprising a plurality of tubes extending away from the first end of the shell towards the second end of the shell. It is contemplated that the tubes from the plurality of tubes have a U-shape.

In at least one embodiment, the ionic liquid reactor further comprises at least one sloped baffle disposed within the shell. Preferably, the baffle is sloped down towards the impeller and the second end of the reactor.

In one or more embodiments, the ionic liquid reactor further comprises a plurality of sloped baffles disposed within the shell and the baffles are sloped down towards the impellers and the second end of the reactor.

In some embodiments, the ionic liquid reactor further comprises a plurality of distributors in communication with the inlet for the hydrocarbon stream and configured to distribute the hydrocarbon stream within the shell. It is contemplated that a plurality of impellers are disposed within the shell. It is further contemplated that a high sheer impeller is disposed below at least one distributor. It is still further contemplated that a high radial mixing impeller is disposed between adjacent distributors. It is also contemplated that a sloped baffle disposed adjacent at least one high shear impeller.

In a second aspect of the present invention, the present invention may be broadly characterized as providing a process for controlling the temperature of an ionic liquid reactor by: injecting an ionic liquid catalyst into a reactor having a shell, the ionic liquid flowing towards a bottom of the shell; injecting a hydrocarbon stream into the reactor, the hydrocarbon stream flowing towards the bottom of the shell; mixing the ionic liquid catalyst and the hydrocarbons in the hydrocarbon stream within the shell so as to promote an exothermic reaction; removing heat from the shell with a heat exchanger disposed within the shell; and, recovering an effluent stream from the reactor.

In at least one embodiment, the injection of the hydrocarbon stream comprises a staged injection.

In one or more embodiments, the mixing of the ionic liquid catalyst and the hydrocarbons is performed by at least one impeller having blades, each blade having a tip. It is contemplated that the hydrocarbon stream is injected into the shell towards the tips of the blades of the at least one impeller.

In some embodiments, the process also includes directing a flow of fluid adjacent to the shell with at least one baffle. It is contemplated that the baffle is sloped down towards impeller blades tips for re-dispersing ionic liquid into fine droplets and for fluid mixing.

In various embodiments, the exothermic reaction is an alkylation reaction.

It is contemplated that the process also includes separating the effluent from the reactor into a hydrocarbon phase and an ionic liquid catalyst phase.

In some of the embodiments, the process includes dispersing the ionic liquid catalyst into fine droplets within the shell with at least one impeller.

In at least one embodiment, the process includes maintaining the effluent in a liquid phase while removing heat from the reaction with the heat exchanger.

Additional aspects, embodiments, and details of the invention are set forth in the following detailed description of the invention.

DETAILED DESCRIPTION OF THE DRAWINGS

In the drawings of the present invention, one or more embodiments are shown in which like numerals denote like elements, and in which.

DETAILED DESCRIPTION OF THE INVENTION

As mentioned above, an ionic liquid catalyst reactor and a process for controlling the heat of an ionic liquid catalyst reaction have been invented which utilize an internal heat exchanger. The heat exchanger in the reactor is designed to accommodate the ionic liquid catalyst, the hydrocarbons, and any conjunct polymer and provide efficient heat exchange while maintaining the reactants and the ionic liquid catalyst in liquid phase. By controlling the heat with the heat exchanger and, more importantly without vaporization, it will be easier to control the reactor operation, ionic liquid dispersion and acid concentration.

With these general principles of the present invention in mind, one or more exemplary embodiments of the present invention will now be described with the understanding that the following is exemplary in nature and is not intended to be limiting.

Figure 1:
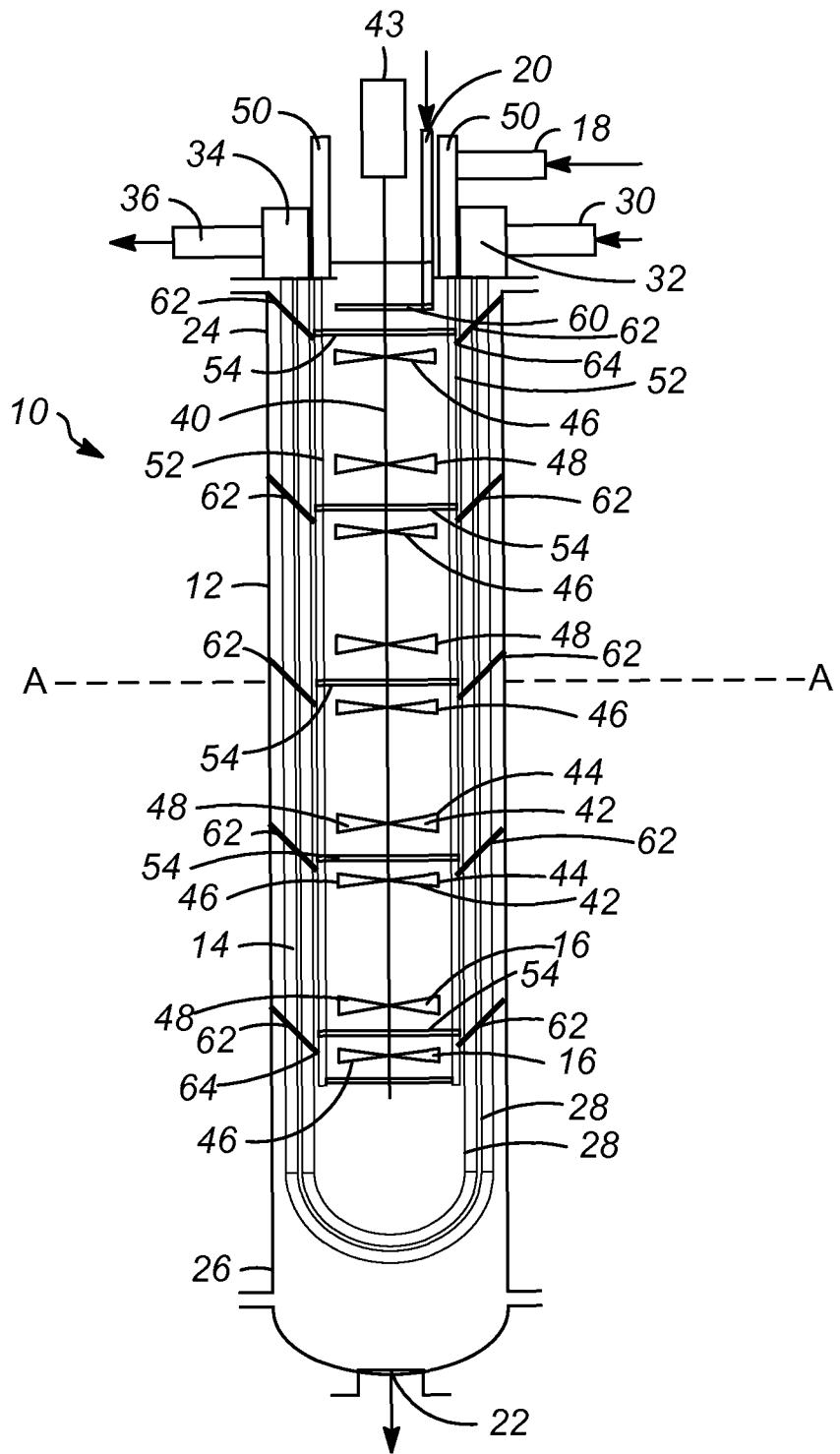
FIG. 1 shows a schematic drawing of a reactor according to one or more embodiments of the present invention.
Figure 2:
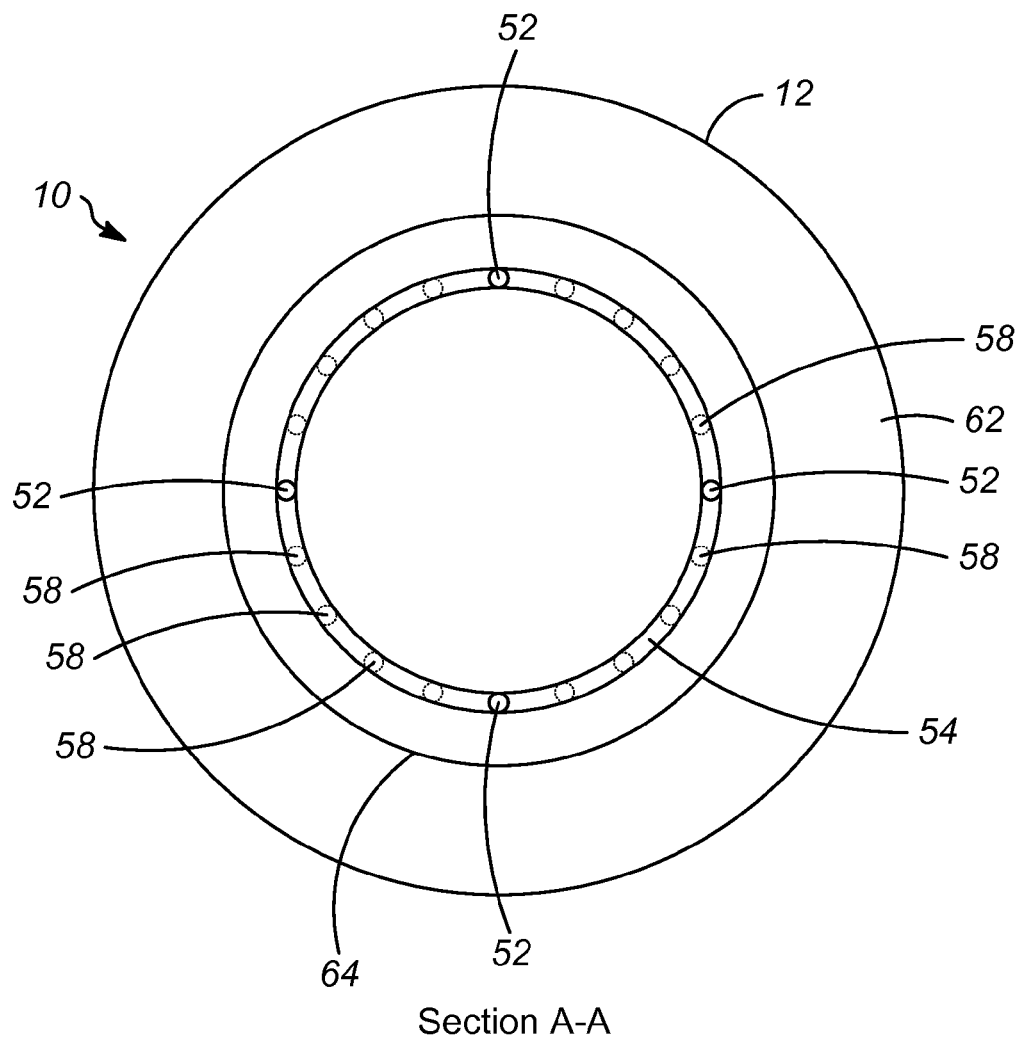
FIG. 2 shows a top view of the reactor in FIG. 1 along line AA with the heat exchange tubes and impellers removed.

As shown in FIGS. 1 and 2, an ionic liquid reactor 10 according to various embodiments of the present invention comprises a shell 12, at least one heat exchanger 14 disposed within the shell 12, and at least one impeller 16 disposed within the shell 12.

The shell 12 comprises an inlet 18 for hydrocarbons, an inlet 20 for ionic liquid catalyst, and an outlet 22 for effluent. The inlet 20 for ionic liquid catalyst and the inlet 18 for hydrocarbons are preferably disposed proximate a first end 24 of the shell 12. Additionally, the outlet 22 for effluent is preferably disposed proximate a second end 26 of the shell 12.

In one or more embodiments, the at least one heat exchanger 14 comprises a plurality of tubes 28. Most preferably, the tubes 28 comprise U-shaped tubes, which extend from the first end 24 towards the second end 26 of the shell 12. Other configurations may also be used. The heat exchanger 14 may further include an inlet 30 for receive a cooling fluid, such as water or a refrigerant, and an inlet manifold 32 for distributing the cooling fluid to the tubes 28. As will be appreciated, the cooling fluid will absorb heat from the fluids within the shell 12 to become heated cooling fluid. The heated cooling fluid will exit the tubes 28, collect in an outlet manifold 34 and pass out of an outlet 36 where the heated cooling fluid may be cooled and re-circulated back or used in other processes for heating.

The reactor 10 includes at least one impeller 16, and preferably a plurality of impellers 16 are disposed within the shell 12. Each impeller 16 may be disposed about a shaft 40 and includes at least one blade 42 extending away from the shaft 40 and terminating in a tip 44. The shaft 40 may be driven by a motor and speed control system 43 so that the rotation of the shaft 40 provides a rotation to the impellers 16. The impellers 16 break ionic liquid into fine droplets, provide fluid mixing for reactions, and distribute the fluid for heat exchange within the shell 12. Different types of impellers 16 may be used. For example, at least one high sheer impeller 46, such as a Rushton impeller, may be used for ionic liquid dispersion as well as for radial fluid mixing. Other impellers that can effectively dispersing ionic liquid into fine droplets and provide effective radial fluid mixing can also be used. It is preferred that the hydrocarbons are injected into the shell 12 in a staged injection. For example, the reactor 10 may include an inlet manifold 50 for hydrocarbons in communication with the inlet 18 for the hydrocarbons. Conduits 52, in communication with the inlet manifold 50 for hydrocarbons, extend downward in the shell 12 towards the second end 26 of the shell 12. A plurality of distributors 54 are disposed at different vertical positions within the shell 12. Each distributor 54 is in communication with the conduits 52 which 52 can be used to support the distributor 54 as well. See, FIG. 2. Preferably, each distributor 54 is disposed above a high sheer impeller 46. It is also preferred that some of the distributors 54 are disposed below a high axial mixing impeller 48 that pumps hydrocarbon reactants and ionic liquid acid catalyst towards the tips of a lower high shear impeller 46.

Figure 3:
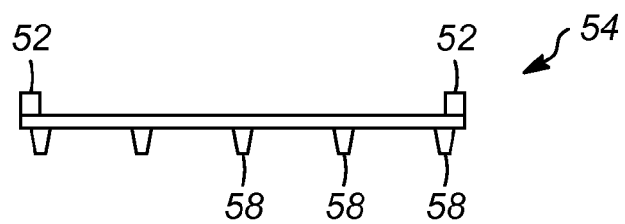
FIG. 3 shows a side view of a ring distributor used for a staged injection of hydrocarbons in one or more embodiments of the present invention; and, FIG. 4 shows a process flow diagram of a process according to one or more embodiments of the present invention.

A preferred distributor 54 is shown in FIG. 3, in which the distributor 54 has a circular shape. The distributor 54 includes a plurality of outlets 58 for injecting the hydrocarbons into the region proximate the tip 44 of the impellers 16. Returning to FIG. 1, in order to facilitate the initial dispersal of ionic liquid within the shell 12, an ionic liquid distributor 60 is in communication with the inlet 20. The ionic liquid distributor 60 can be similar in design to the distributor 54 shown in FIG. 2.

As discussed above, due to the different densities, the ionic liquid and the hydrocarbons will separate. Accordingly, the reactor 10 preferably includes at least one baffle 62 to direct the flow of fluids, especially ionic liquid, in the shell 12 back to impellers 16 within the shell 12 of the reactor 10 for dispersion and mixing. Preferably, there are a plurality of baffles 62 that are spaced apart within the shell 10 so that there is a space between adjacent baffles 62 such that fluids can flow between adjacent baffles.

Most preferably, the baffles 62 are sloped towards the impellers 16 and the second end 26 or bottom of the shell 12. Thus, any fluids, and particularity any ionic liquid, will flow towards the bottom and more importantly towards the center of the shell 12—which is towards the impellers 16 and the distributors 54. In addition to increasing the mixing between the ionic liquid and the hydrocarbons, this will avoid the separation of ionic liquid from hydrocarbons injected through the distributors 54 with the shell 12 of the reactor 10. The baffles 62 may terminate at an end 64 proximate a distributor 54 near the tips 44 of an impeller 16, for example the high sheer impeller 46 disposed below the distributor 54. The foregoing arrangement of impellers 16, hydrocarbon distributors 54, and slopped baffles 62 is for quickly mixing hydrocarbon reactants and dispersion of the ionic liquid acid catalyst, as well as for minimizing localized concentration of reactants, especially olefins, to facilitate the desired alkylation reaction. Other configurations may be utilized in accordance with the present invention. In a preferred embodiment, the reactor 10 is utilized for an alkylation reaction, and therefore the use of a preferred embodiment of the present invention will be described in relation to an alkylation reaction, with the understanding that the present invention is not necessarily limited to same and can be practiced in association with different exothermic reactions.

Figure 4:
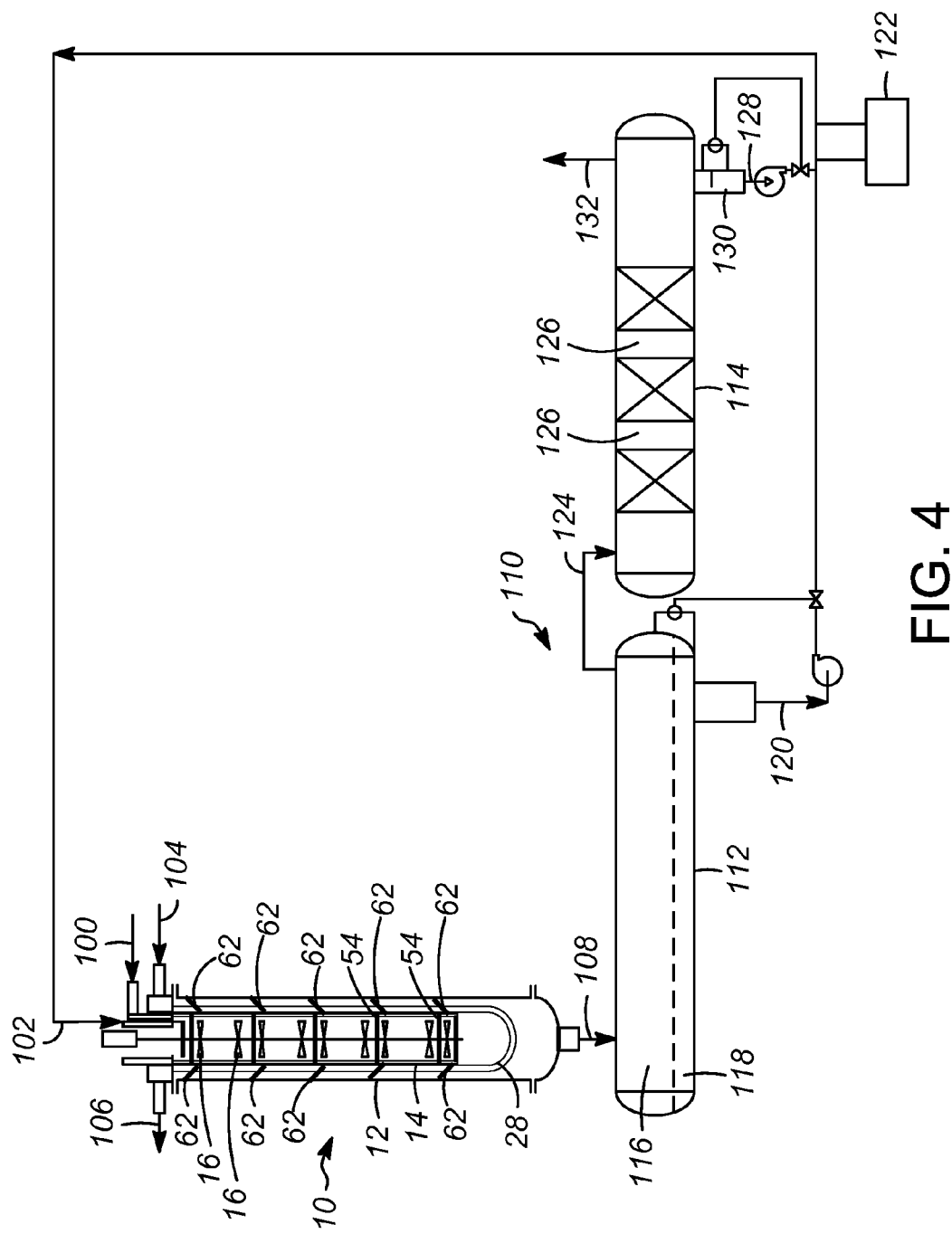

With reference to FIG. 4, a hydrocarbon stream 100 comprising iC$_4$ hydrocarbons and olefins is passed into the reactor 10. The olefinic hydrocarbons are preferably the limiting reagent in the reaction. An ionic liquid catalyst stream 102 is also passed into the reactor 10, preferably in a co-current manner.

In order to mix the ionic liquid catalyst and the hydrocarbons, the impellers 16 in the reactor 10 will rotate. The impellers 16, together with slopped baffles 62, will mix the reactants and the ionic liquid catalyst within the shell 12. Additionally, the impellers 16 will disperse the ionic liquid by breaking the ionic liquid into small droplets. In the reactor 10, which is operated under proper conditions, with a temperature preferably between 4.4° to 37.8° C. (40° to 100° F.) and a pressure sufficient to keep the reactants and catalyst in liquid phase, the olefinic hydrocarbons will react with the iC$_4$ hydrocarbons to form alkylated hydrocarbons, primarily iso-octane and other trimethylpentanes.

As the reactions occur, a cooling fluid 104 may be passed through the tubes 28 of the heat exchanger 14 and absorb heat. A heated cooling fluid 106 may be cooled or passed from the reactor 10 to another process to provide heat and then re-circulated back to the heat exchanger 14. The baffles 62 will direct the ionic liquid, and other fluid(s), towards the impellers 16 in the center of the shell 12 of the reactor 10 where the ionic liquid is dispersed into fine droplets and the fluids can be mixed by the impellers 16 and catalyze new reactants injected into the shell 12 via the distributors 54. Eventually, the fluids in the shell 12 will flow downward and reach the bottom of the shell 12 of the reactor 10.

An effluent stream 108 from the reactor 10 may be passed to a separation zone 110 which can include, for example, two vessels 112, 114. In a first separation vessel 112, the effluent mixture will separate into a lighter hydrocarbon phase 116 and a heavier, ionic liquid catalyst phase 118. Preferably, in the first separation vessel 112, at least 50%, and more preferably at least 90% of the ionic liquid catalyst will be separated from the hydrocarbons due to the different densities of the phases. The ionic liquid catalyst phase 118 can be withdrawn in a spent ionic liquid catalyst stream 120, which can be reused in the process, which can be regenerated in a regeneration zone 122, which can be disposed of, or a combination thereof. The hydrocarbon phase 116 can be withdrawn in a hydrocarbon effluent stream 124 which may be passed to the second separation vessel 114.

In the second separation vessel 114, entrained fine droplets of ionic liquid catalyst within the hydrocarbon phase 116 from the first separation vessel 112 may be further separated by gravity as well as with other means, for example with a coalescer material 126, such as glass beads, fibers or with an electrostatic separation device. A second spent ionic liquid catalyst stream 128 comprising ionic liquid catalyst 130 separated in the second separation vessel 114 can be combined with the spent ionic liquid catalyst stream 120 from the first separation vessel 112. A hydrocarbon product stream 132, in this case comprising an alkylate product, can be passed from the second separation vessel 114 to a fractionation column (not shown) or other separation unit to separate the various hydrocarbons in the product stream, which may include unreacted reactants that may be recycled to the reactor 10.

By using the heat exchanger in the reactor, a better temperature control may be provided. Moreover, by utilizing the slopped baffles, ionic liquid is directed back into impeller tip zones for dispersion and for mixing with hydrocarbon reactants. The arrangement of slopped baffles, impellers and reactant distributors will allow for the fluid mixing and heat exchange to be effective and remain effective.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for controlling a temperature of an ionic liquid reactor used for alkylation of hydrocarbons comprising paraffins with olefins, the process comprising:
    injecting an ionic liquid catalyst into a vertical reactor having a shell, the ionic liquid flowing towards a bottom of the shell;
    injecting the hydrocarbons into the reactor with a distributor, the distributor comprising a circular shape, a plurality of outlets for dispersing the hydrocarbons within the shell, and a conduit extending downward through the shell, the conduit supporting the distributor and providing the hydrocarbons to the distributor, the hydrocarbons flowing towards the bottom of the shell;
    mixing the ionic liquid catalyst and hydrocarbons within the shell so as to promote an alkylation reaction between paraffins and olefins to form alkylated hydrocarbons and conjunct polymers including highly conjugated, olefinic, highly cyclic hydrocarbons, wherein mixing of the ionic-liquid catalyst and the hydrocarbons from the hydrocarbon stream is performed by at least one impeller having blades, each blade having a tip;
    directing a flow of fluid adjacent to the shell of the vertical reactor with at one baffle wherein the at least one baffle extends from the shell towards a center of the reactor, and wherein the at least one baffle is sloped towards a bottom of the shell of the vertical reactor;
    removing heat with a heat exchanger disposed within the shell; and
    recovering an effluent stream from the reactor.

2. The process of claim 1, wherein the injection of the hydrocarbon stream comprises a staged injection.

3. The process of claim 1 further comprising:
    injecting the hydrocarbon stream into the shell towards the tips of the blades of the at least one impeller.

4. The process of claim 1 further comprising:
    separating the effluent stream from the reactor into a hydrocarbon phase and an ionic liquid catalyst phase.

5. The process of claim 1 further comprising:
    dispersing the ionic liquid catalyst into fine droplets within the shell with at least one impeller.

6. The process of claim 1 further comprising:
maintaining the effluent stream in a liquid phase while removing heat from the reactor with the heat exchanger.
7. The process of claim 1 wherein the baffle directs the flow of fluids towards the at least one impeller.

* * * * *